(12) United States Patent
Taylor et al.

(10) Patent No.: US 10,376,338 B2
(45) Date of Patent: Aug. 13, 2019

(54) SURGICAL ROBOTIC ARM SUPPORT SYSTEMS AND METHODS OF USE

(71) Applicant: Covidien LP, Mansfield, MA (US)

(72) Inventors: Eric Taylor, East Hampton, CT (US); Josh Snow, Clinton, CT (US); Peter Hathaway, Lebanon, CT (US); Michael Stow, Hamden, CT (US); Russell Pribanic, Roxbury, CT (US); Andrew Miesse, Durham, CT (US); Christopher Switalski, Suffield, CT (US); Michael Zemlok, Prospect, CT (US); Jason Iceman, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 227 days.

(21) Appl. No.: 15/310,564

(22) PCT Filed: Apr. 29, 2015

(86) PCT No.: PCT/US2015/028210
§ 371 (c)(1),
(2) Date: Nov. 11, 2016

(87) PCT Pub. No.: WO2015/175218
PCT Pub. Date: Nov. 19, 2015

(65) Prior Publication Data
US 2017/0071693 A1 Mar. 16, 2017

Related U.S. Application Data

(60) Provisional application No. 61/992,277, filed on May 13, 2014.

(51) Int. Cl.
*G05B 19/00* (2006.01)
*A61B 90/50* (2016.01)
(Continued)

(52) U.S. Cl.
CPC .............. *A61B 90/50* (2016.02); *A61B 34/30* (2016.02); *B25J 9/0009* (2013.01); *B25J 9/009* (2013.01);
(Continued)

(58) Field of Classification Search
CPC .... A61B 17/00234; A61B 2017/00482; A61B 34/30; A61B 90/50; A61B 90/90;
(Continued)

(56) References Cited

U.S. PATENT DOCUMENTS 5,748,767 A 5/1998 Raab
5,762,458 A 6/1998 Wang et al.
(Continued)

FOREIGN PATENT DOCUMENTS

DE 202008009571 U1 10/2008
DE 102014203921 A1 9/2015
(Continued)

OTHER PUBLICATIONS

European Search Report dated Dec. 20, 2017, corresponding to European Application No. 15793145.2; 9 total pages.
(Continued)

*Primary Examiner* — Harry Y Oh (57) ABSTRACT

A surgical robotic arm support system may include a base and at least one post and/or a connection for coupling a robot arm to the support system. The base may be configured to at least partially surround a surgical table. The at least one post may have a first end supported on the base and a second end configured to support a robotic arm. The at least one post may be configured to be coupled to a surgical table. The connection may support a mechanical and/or electrical connectivity between the support system and a coupled robot arm. Electrical connectivity may be configured to identify at least one of the robot arm connections to which at least one
(Continued)

robot arm is connected. Each robot arm connection may be configured to maintain a portion of a connected robot arm at a predetermined position from the base.

21 Claims, 6 Drawing Sheets (51) Int. Cl.
| | |
|---|---|
| A61B 34/30 | (2016.01) |
| B25J 9/00 | (2006.01) |
| B25J 9/08 | (2006.01) |
| B25J 9/16 | (2006.01) |
| B25J 19/00 | (2006.01) |
| A61B 17/00 | (2006.01) |
| A61B 90/90 | (2016.01) |

(52) U.S. Cl.
CPC .............. *B25J 9/08* (2013.01); *B25J 9/1669* (2013.01); *B25J 9/1697* (2013.01); *B25J 19/0045* (2013.01); *A61B 17/00234* (2013.01); *A61B 90/90* (2016.02); *A61B 2017/00482* (2013.01); *Y10S 901/09* (2013.01); *Y10S 901/27* (2013.01)

(58) Field of Classification Search
CPC ...... B25J 19/0045; B25J 9/0009; B25J 9/009; B25J 9/08; B25J 9/1669; B25J 9/1697; Y10S 901/09; Y10S 901/27
See application file for complete search history.

(56) References Cited

U.S. PATENT DOCUMENTS

| | | | |
|---|---|---|---|
| 6,063,095 A | 5/2000 | Wang et al. | |
| 6,076,525 A | 6/2000 | Hoffman | |
| 6,102,850 A * | 8/2000 | Wang | B25J 9/1689 |
| | | | 414/2 |
| 6,470,236 B2 * | 10/2002 | Ohtsuki | B25J 9/1689 |
| | | | 345/157 |
| 6,788,018 B1 | 9/2004 | Blumenkranz | |
| 7,035,716 B2 | 4/2006 | Harris et al. | |
| 7,682,357 B2 * | 3/2010 | Ghodoussi | G06F 19/3418 |
| | | | 606/1 |
| 7,797,157 B2 | 9/2010 | Anvari | |
| 7,954,397 B2 | 6/2011 | Choi et al. | |
| 7,979,157 B2 | 7/2011 | Anvari | |
| 8,392,022 B2 | 3/2013 | Ortmaier et al. | |
| 9,446,177 B2 * | 9/2016 | Millman | A61M 1/0058 |
| 2002/0091374 A1 * | 7/2002 | Cooper | A61B 46/13 |
| | | | 606/1 |
| 2003/0040758 A1 | 2/2003 | Wang et al. | |
| 2003/0109780 A1 * | 6/2003 | Coste-Maniere | B25J 9/1671 |
| | | | 600/407 |
| 2004/0128026 A1 | 7/2004 | Harris et al. | |
| 2006/0149418 A1 * | 7/2006 | Anvari | A61G 13/10 |
| | | | 700/245 |
| 2009/0326318 A1 * | 12/2009 | Tognaccini | A61B 1/00183 |
| | | | 600/104 |
| 2010/0204713 A1 * | 8/2010 | Ruiz Morales | B25J 9/041 |
| | | | 606/130 |
| 2010/0331859 A1 * | 12/2010 | Omori | A61B 17/4241 |
| | | | 606/130 |
| 2011/0022060 A1 | 1/2011 | Won et al. | |
| 2011/0190937 A1 | 8/2011 | Ortmaier | |
| 2012/0029694 A1 | 2/2012 | Muller | |
| 2012/0041263 A1 | 2/2012 | Sholev | |
| 2013/0096575 A1 | 4/2013 | Olson | |
| 2013/0144307 A1 | 6/2013 | Jeong et al. | |
| 2013/0304086 A1 | 11/2013 | Tovey et al. | |
| 2013/0325033 A1 | 12/2013 | Schena et al. | |
| 2014/0314538 A1 * | 10/2014 | Carter | A61B 90/50 |
| | | | 414/744.3 |
| 2017/0079731 A1 * | 3/2017 | Griffiths | A61B 34/30 |

FOREIGN PATENT DOCUMENTS

| | | |
|---|---|---|
| WO | 9937220 A1 | 7/1999 |
| WO | 2006/079108 A1 | 7/2006 |
| WO | WO 2010-008126 | 1/2010 |
| WO | 2010068005 A2 | 6/2010 |
| WO | WO 2010-068005 | 6/2010 |

OTHER PUBLICATIONS

European Search Report dated Dec. 7, 2017, corresponding to European Application No. 15792219.6; 10 pages.
International Search Report for (PCT/US2015/028210) date of completion is Aug. 4, 2015 (3 pages).
Chinese Office Action (with English translation) dated Aug. 21, 2018, corresponding to Chinese Application No. 201580025231.0; 15 total pages.

* cited by examiner

SURGICAL ROBOTIC ARM SUPPORT SYSTEMS AND METHODS OF USE

CROSS-REFERENCE TO RELATED APPLICATIONS

This application is a U.S. National Stage Application filed under 35 U.S.C. § 371(a) of International Patent Application No. PCT/US2015/028210, filed Apr. 29, 2015, which claims the benefit of and priority to U.S. Provisional Patent Application No. 61/992,277, filed May 13, 2014, the entire disclosure of which is incorporated by reference herein.

BACKGROUND

Robotic surgical systems have been used in minimally invasive medical procedures. Some robotic surgical systems include a console and multiple robot arms. Surgical instruments that included an end effector, such as forceps or a grasping tool, were mountable to one or more of the robot arms. The robot arms provided mechanical power to a surgical instrument for its operation and movement. Each robot arm may include an instrument drive unit that is operatively connected to the surgical instrument.

Robotic surgical systems have included three or more robots arms usable during surgery. These arms were positioned at different locations alongside a patient to enable the instruments at the end of the arms to be inserted in different trocars. In some instances each of the arms were mounted directly to the surgical table on which the patient was positioned for surgery. In other instances the arms were mounted to movable carts that were wheeled to a desired position alongside the surgical table.

These mounting options required the use of position sensors and other components to identify the location of each arm relative to the other arms and/or a camera during the positioning of the arms. This added to the cost and complexity of the robot arms. Additionally, it was difficult to create a universal interface for securely mounting the robot arms to different types of surgical tables to prevent the arms from inadvertently moving during surgery.

There is a need for positioning surgical robot arms in a way that the relative position of each arm to the other arms and/or a camera may be ascertained without additional position sensors or other components. There is also a need for securely fixing the position of the robot arms independent of the surgical table being used so that the arms are less likely to move during surgery.

SUMMARY

A robotic arm support system may be initially positioned on the floor alongside a surgical table. The support system may have a shape contoured to one or more parts of the surgical table. The arm support system may include two or more electrical and/or mechanical connections for electrically and/or mechanically connecting each of the robot arms to the arm support system. Each of the connections may be located at a known distance from the other connections on the arm support system. These known distances may be used to quickly calculate the relative position of each arm connected to the support system without the need for additional position sensors.

The electrical connections may also be used to transmit power, instructions, and signals to and from each robotic arms. This may eliminate the need for additional electrical cables running along the floor of the operating room to each of robot arms. These additional cables could pose a tripping hazard to the operating room staff.

The support system may have a U-shape, L-shape, O-shape, or other shape that at least partially surrounds the bed. The support system may include modular pieces that can be coupled together once the bed has been positioned in the surgical suite. The modular pieces may also be preassembled and/or pre-positioned in the operating room and the surgical table may be then moved into a desired position relative to the support system. The modular pieces may be adjustable to accommodate different surgical table sizes and types.

A surgical robotic arm support system may include a base configured to at least partially surround a surgical table, two or more robot arm connections on the base, and an electrical connectivity configured to identify at least one of the robot arm connections to which at least one robot arm is connected. The electrical connectivity may be disposed between the connected robot arm and the base.

Each robot arm connection may be configured to maintain a portion of a connected robot arm at a predetermined position from the base. Each robot arm connection may include a mechanical connectivity restricting movement of at least part of the connected robot arm relative to the base.

A memory may be included and may be configured to store location information of two or more of the robot arm connections. A processing unit may be included and configured to calculate a position of at least two robot arms connected to different robot arm connections from the stored location information. The processing unit may be configured to align a movement of an input device of the surgical robotic arm support system with a corresponding movement of an instrument affixed to a robotic arm or a displayed image from a camera coupled to one of the robot arms based on the calculated position.

The electrical connectivity may be configured to identify at least one of the robot arm connections from a unique identifier associated with the at least one robot arm connection, to detect a robot arm coupling, and/or to identify a particular robot arm coupled to the at least one robot arm connection.

The base may include at least one modular link selectively attachable to at least one other modular link.

The base may include more than one link, and in some instances may include at least three modular links. At least one modular link may have a longitudinal axis that is perpendicular to longitudinal axes of at least two of the other modular links when the at least three modular links are attached together.

In some instances, at least one modular link may be axially movable along its respective longitudinal axis to adjust a dimension of the base. In some instances, each of the modular links may be axially movable along their respective longitudinal axes to adjust at least a width and a length of the base.

A method may include connecting a surgical robotic arm to at least one of two or more robotic arm connections on a surgical robotic arm support system base and identifying the at least one robotic arm connection to which the surgical robotic arm is connected. The surgical robotic arm support system base may be configured to at least partially surround a surgical table.

Movement of at least part of the connected robotic arm relative to the base may be mechanically restricted as part of the connecting the surgical robotic arm to the at least one robotic arm connection. Electrical connectivity may be enabled between the connected robotic arm and the surgical robotic arm support system base as part of the connecting the robotic arm to the at least one robotic arm connection.

A position of at least two robotic arms connected to different robotic arm connections may be calculated from location information about the robotic arm connections stored in a memory.

Movement of an input device of the surgical robotic arm support system may be aligned with a corresponding movement of an instrument or camera affixed to one of the connected robotic arms based on the calculated position.

Circuitry enabling an electrical connectivity between a robotic arm and the robotic arm connection to which the arm is connected may enable identification of each of the connected robotic arms and the robot arm connection to which each identified robotic arm is connected.

Two or more modular links may be coupled together around the surgical table to form the surgical robotic arm support system base. At least one of the modular links may be axially moved along its respective longitudinal axis to adjust a dimension of the base relative to the surgical table.

A signal from a position sensor configured to detect a movement of at least one of the links may be processed by a processing device. An amount of detected movement of the at least one link may be identified from the processing. The identified amount of detected movement may be compared to a threshold value. A notification may be triggered when the compared amount exceeds the threshold value.

A surgical robotic arm support system may include a base configured to at least partially surround a surgical table. The support system may also include at least one post having a first end supported by a mechanical and/or electrical connection on the base and a second end supporting a robotic arm. The post may be considered to be part of the robotic arm or it may be a separate component that is detachable from the robotic arm.

The base may include a plurality of links connected to one another and selectively adjustable relative to one another. Each link may include one or more electrical and/or mechanical connections to which a robotic arm may be connected. The plurality of links may include a first L-shaped link and a second L-shaped link. The first L-shaped link may have a first leg and a second leg. The second L-shaped link may have a first leg and a second leg. The first legs of the first and second L-shaped links may be connected to one another and define a first axis therethrough. The first and second L-shaped links may be movable relative to one another along the first axis to adjust a width of the base.

In embodiments, the plurality of links may further include a first linear link and a second linear link. The first linear link may be connected to the second leg of the first L-shaped link. A second axis, perpendicular to the first axis, may be defined through the first linear link and the second leg of the first L-shaped link. The first linear link may be movable relative to the second leg of the first L-shaped link along the second axis to adjust a length of the base. The second linear link may be connected to the second leg of the second L-shaped link. A third axis, perpendicular to the first axis, may be defined through the second linear link and the second leg of the second L-shaped link. The second linear link may be movable relative to the second leg of the second L-shaped link along the third axis.

The base may have a rectangular configuration.

In some instances, a post may include a joint movably connecting the first and second ends thereof to one another. The first and second ends of the at least one post may be movable relative to one another along an axis defined along the at least one post. The joint may be configured to be slidingly coupled to a rail of a surgical table.

In embodiments, one of the first and second ends of the at least one post is configured to be slidingly coupled to a rail of a surgical table. The first end of the at least one post may be pivotably coupled to the base.

In another aspect of the present disclosure, a method of supporting surgical robotic arms is provided. The method includes providing a surgical robotic arm support system. The support system includes a base, at least one first post, and at least one second post. The base is configured to at least partially surround a surgical table. Each of the posts has a first end supported on the base and a second end configured to support a robotic arm. The posts are configured to be coupled to a surgical table. The method further includes: positioning the base of the support system to at least partially surround a surgical table; coupling the at least one first post to a first rail of the surgical table; coupling the at least one second post to a second rail of the surgical table; and coupling a robotic arm to the second end of each post.

In embodiments, the method may further include selectively adjusting at least one of a width or a length of the base of the support system. The method may further include axially moving a plurality links of the base relative to one another. Each of the plurality of links may support a respective post thereon. The plurality of links of the base may include a first L-shaped link and a second L-shaped link. The first L-shaped link may have a first leg and a second leg. The second L-shaped link may have a first leg and a second leg. The first legs of the first and second L-shaped links may be connected to one another and define a first axis therethrough. The method may further include moving the first and second L-shaped links relative to one another along the first axis to adjust a width of the base.

In embodiments, the plurality of links of the base may further include a first linear link and a second linear link. The first linear link may be connected to the second leg of the first L-shaped link. A second axis, perpendicular to the first axis, may be defined through the first linear link and the second leg of the first L-shaped link. The second linear link may be connected to the second leg of the second L-shaped link. A third axis, perpendicular to the first axis, may be defined through the second linear link and the second leg of the second L-shaped link. The method may further include moving the first linear link relative to the second leg of the first L-shaped link along the second axis to adjust a first length of the base; and moving the second linear link relative to the second leg of the second L-shaped link along the third axis to adjust a second length of the base.

In embodiments, the method may further include adjusting a configuration of the base to correspond to a profile of the surgical table.

In some aspects of the present disclosure, the method may further include moving a first end of each post relative to a second end of each post about a respective joint thereof. The method may further include moving the first and second ends of each post relative to one another along an axis extending along a respective post.

It is contemplated that the method may further include sliding the second ends of each post along a rail of the surgical table. The method may further include pivoting the first end of each post relative to the base.

The method may also include processing a signal from a position sensor configured to detect a movement of at least one of the links and/or a signal from an angular sensor configured to identify an angular alignment change of at least one post or robotic arm. An amount of detected movement may be identified from the processed linear sensor signal. An amount of angular alignment change of the at least one post or robotic arm may be identified from the processed angular sensor signal. The identified amount of detected movement and/or the amount of angular alignment change may be compared to one or more respective threshold values. One or more notifications may be triggered when one or more of the compared amounts exceed their respective threshold values.

In yet another aspect of the present disclosure, another embodiment of a surgical robotic arm support system is provided. The support system includes a base and a plurality of posts. The base has a rectangular configuration configured to at least partially surround a surgical table. The base includes first, second and third links. The first link has a first end and a second end and defines a first axis therebetween. The second link is movably coupled to the first end of the first link and defines a second axis therealong. The second axis is perpendicular to the first axis. The second link is axially movable relative to the first link along the second axis to adjust a first length of the base. The third link is movably coupled to the second end of the first link and defines a third axis therealong. The third axis is perpendicular to the first axis. The third link is axially movable relative to the first link along the third axis to adjust a second length of the base. Each post of the plurality of posts is supported on one of the second and third links of the base and configured to be coupled to a robotic arm. The plurality of posts is configured to be coupled to a surgical table. Each post of the plurality of posts includes a joint.

In embodiments, the first and second ends of the first link may be axially movable relative to one another along the first axis to adjust a width of the base.

In embodiments, a surgical robotic arm support system may include a base configured to at least partially surround a surgical table and two or more robot arm connections on the base. Each robot arm connection may maintain a portion of a connected robot arm at a predetermined position from the base. The surgical robotic arm support system may also include a detector identifying at least one of the robot arm connections to which at least one robot arm is connected.

Each robot arm connection may include a mechanical connectivity restricting movement of at least part of the connected robotic arm relative to the base. Each robot arm connection may also include an electrical connectivity between the connected robot arm and the surgical robotic support system.

The surgical robotic support system may also include a memory storing location information of two or more of the robot arm connections. The surgical robotic support system may also include a processing unit configured to calculate a position of at least two robot arms connected to different robot arm connections from the location information stored in the memory.

The processing unit may be further configured to align a movement of an input device of the surgical robotic support system with a corresponding movement of an instrument affixed to a robotic arm or a displayed image from a camera coupled to one of the robot arms. This alignment may be determined from the calculated positions of the robot arms.

The detector may include circuitry configured to identify at least one of the robot arm connections from a unique identifier associated with the at least one robot arm connection. The detector may include a sensor at the at least one robot arm connection. The sensor may be configured to detect a robot arm coupling to the connection. The sensor may also be configured to identify a particular robot arm coupled to the at least one robot arm connection.

The base of the surgical robotic support system may include at least one modular link selectively attachable to at least one other modular link. In some instances, the base may include at least three modular links with at least one modular link having a longitudinal axis that is perpendicular to longitudinal axes of at least two other modular links when the three modular links are attached together.

At least one of the modular links may be axially movable along its respective longitudinal axis to adjust a dimension of the base. In some instances, each of the modular links may be axially movable along their respective longitudinal axes to adjust at least a width and a length of the base.

A surgical robot arm may be connected to at least one of two or more robot arm connections on a surgical robot arm support system base. The base may be configured to at least partially surround a surgical table. The robot arm connection to which the surgical robot arm is connected may be automatically identified using sensors, logic, detectors, circuitry, or other devices.

Part of the connecting the surgical robot arm to the at least one robot arm connection may include mechanically restricting movement of at least part of the connected robot arm relative to the base. Part of the connecting the robot arm to the at least one robot arm connection may include enabling electrical connectivity between the connected robot arm and the surgical robotic support system.

A position of at least two robot arms connected to different robot arm connections may be automatically calculated from stored location information about the robot arm connections. A movement of an input device of the surgical robotic support system may be automatically aligned with a corresponding movement of an instrument or camera affixed to one of the connected robotic arms based on the calculated position.

Each of the connected robot arms and the robot arm connection to which each identified robot arm is connected may be automatically identified using sensors, logic, detectors, circuitry, or other devices.

Two or more modular links may be coupled together around the surgical table to form the surgical robot arm support system base. At least one of the modular links may be axially moved along its respective longitudinal axis to adjust a dimension of the base relative to the surgical table.

The surgical robotic arm support system may include at least one linear sensor and/or at least one angular sensor. The linear sensor may be configured to identify a positional change resulting from a movement of at least one of the links. A processing device may be configured to trigger a notification when the identified positional change exceeds a threshold value.

The angular sensor may be configured to identify an angular alignment change of at least one post or robotic arm. A processing device may be configured to trigger a notification when the identified angular alignment change exceeds a threshold value.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein.

As used herein, the terms parallel and perpendicular are understood to include relative configurations that are substantially parallel and substantially perpendicular up to about + or −10 degrees from true parallel and true perpendicular.

DETAILED DESCRIPTION

Embodiments of the presently disclosed surgical robotic support systems and methods of use thereof are described in detail with reference to the drawings, in which like reference numerals designate identical or corresponding elements in each of the several views. As used herein the term "distal" refers to that portion of the support system that is farther from a floor on which the support system is positioned, while the term "proximal" refers to that portion of the support system that is closer to the floor.

Figure 1:
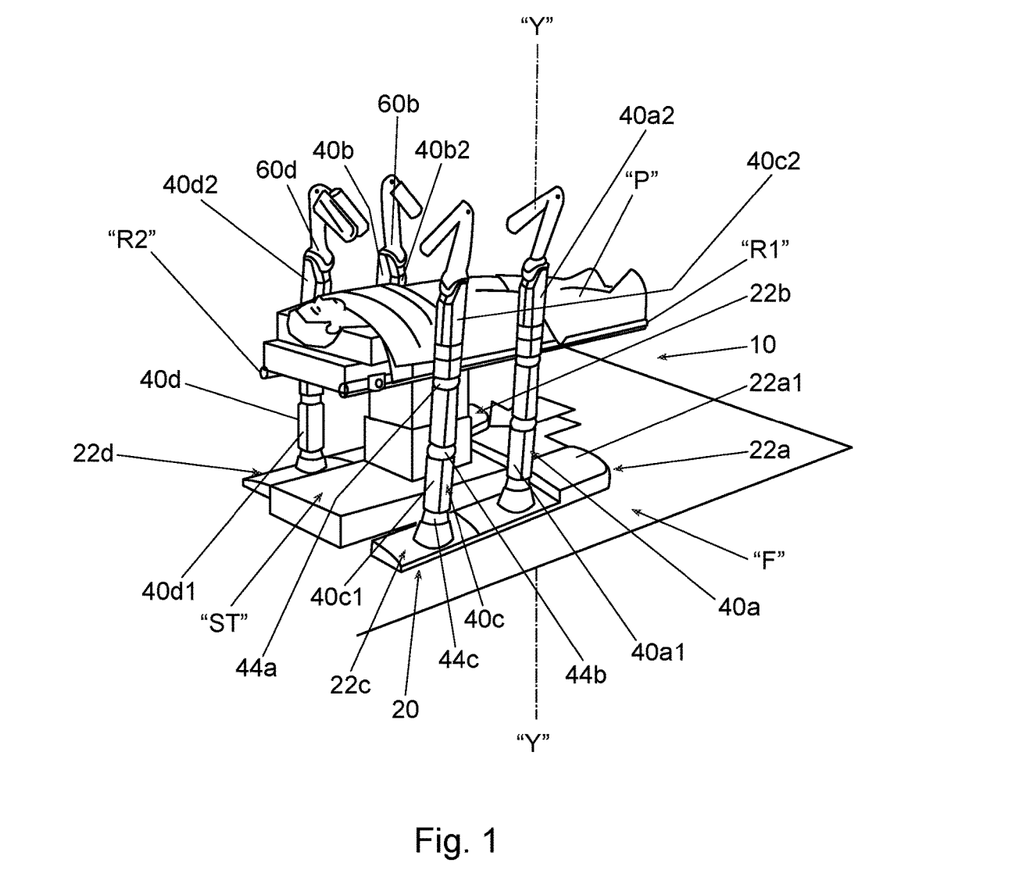
FIG. 1 is a perspective view of a first exemplary surgical robotic support system and a surgical table.
Figure 2:
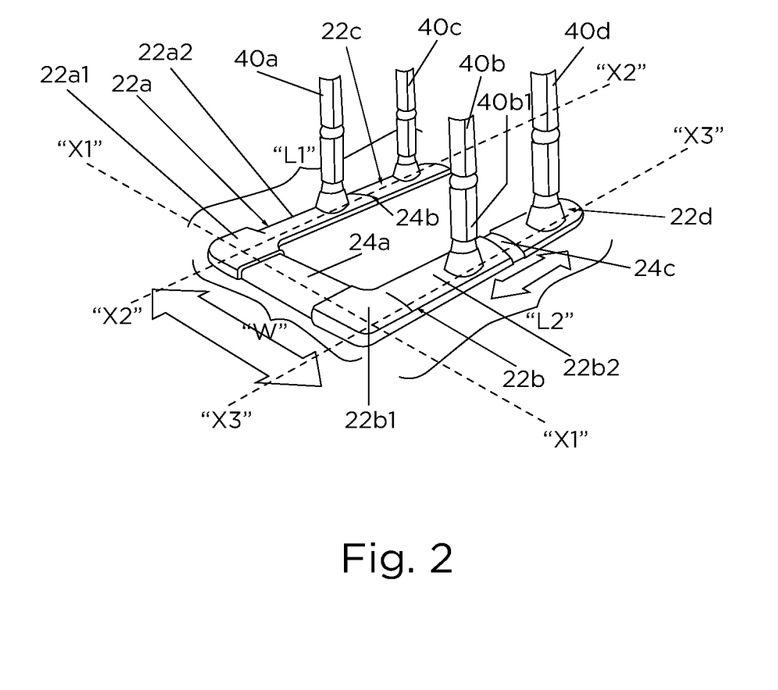
FIG. 2 is a cutaway view of the support system shown in FIG. 1.
Figure 3:
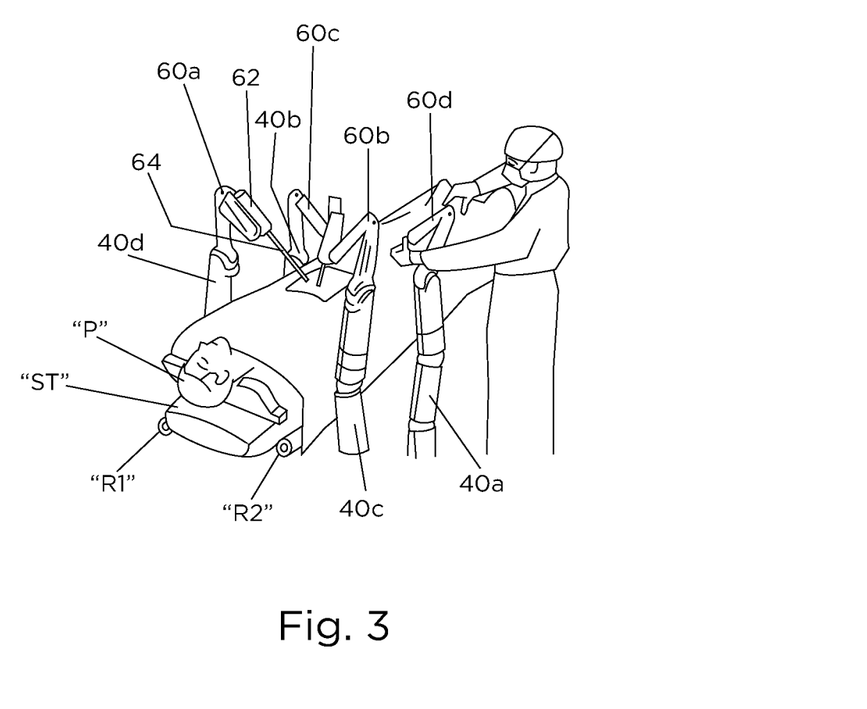
FIG. 3 is a perspective view of the support system shown in FIG. 1 illustrating a surgical procedure.

Turning to FIGS. 1-3, a surgical robotic arm support system 10 is provided. Support system 10 is configured to be positioned on a floor "F" of an operating room and to at least partially surround a surgical table "ST." Support system 10 generally includes a base 20 and a plurality of posts 40a, 40b, 40c, 40d extending perpendicularly and upwardly from base 20. As described in greater detail below, each post 40a, 40b, 40c, 40d is configured to support a robotic arm 60a, 60b, 60c, 60d therein or thereon and to be coupled to surgical table "ST."

Base 20 of support system 10 is sized and dimensioned to at least partially surround surgical table "ST." Base 20 has a generally rectangular configuration configured to accommodate or border a perimeter of surgical table "ST." It is contemplated that base 20 can be variously configured to match the profile of, or at least partially surround, variously dimensioned surgical tables. For example, in some embodiments, base 20 may be circular, oval, square, triangular, ellipsoid, polygonal, uniform, non-uniform and/or tapered. As such, some or all of the various components forming base 20 may have linear, arcuate, or other profiles as needed or desired.

Base 20 includes a plurality of links, for example, a first L-shaped link 22a, a second L-shaped link 22b, a first linear link 22c, and a second linear link 22d connected to one another and selectively adjustable relative to one another to adjust an overall width and an overall length of base 20. As such, the dimensions of base 20 can be adjusted to better accommodate a particular size of a surgical table, a size of a patient resting on the surgical table, and/or a surgeons preference. Further, posts 40a, 40b, 40c, 40d, which are attached to corresponding links 22a, 22b, 22c, 22d, can be moved between a plurality of selected positions relative to surgical table "ST" via relative movement of the plurality of links 22a, 22b, 22c, 22d.

First and second L-shaped links 22a, 22b each include a first leg 22a1, 22b1 and a second leg 22a2, 22b2. First legs 22a1, 22b1 are connected to respective second legs 22a2, 22b2 such that L-shaped links 22a, 22b together form a substantially squared configuration. First legs 22a1, 22b1 of L-shaped links 22a, 22b define a first longitudinal axis "X1" (see FIG. 2) therethrough. First legs 22a1, 22b1 have an adjustable length configured to correspond to a width of surgical table "ST." First legs 22a1, 22b1 are movable relative to one another along first longitudinal axis "X1." Specifically, first legs 22a1, 22b1 can be moved relative to one another between an approximated position and various spaced apart positions.

Base 20 includes a first coupling portion 24a interconnecting first legs 22a1, 22b1 of corresponding first and second L-shaped links 22a, 22b such that relative positions of first legs 22a1, 22b1 can be selectively adjusted. In some embodiments, first coupling portion 24a may be in the form of a telescoping feature or nested tubes slidingly disposed with one another. It is further contemplated that first legs 22a1, 22b1 of respective first and second L-shaped links 22a, 22b are movably connected to one another via various fastening engagements, such as, for example, threading engagement.

First linear link 22c is connected to second leg 22a2 of first L-shaped link 22a. A second longitudinal axis "X2" (see FIG. 2), perpendicular to the first longitudinal axis "X1," is defined through first linear link 22c and second leg 22a2 of first L-shaped link 22a. First linear link 22c is movable relative to second leg 22a2 of first L-shaped link 22a along the second longitudinal axis "X2" to adjust a first length "L1" of base 20. Base 20 includes a second coupling portion 24b, similar to first coupling portion 24a, interconnecting first linear link 22c and second leg 22a2 of first L-shaped link 22a such that relative positions of first linear link 22c and second leg 22a2 of first L-shaped link 22a can be selectively adjusted. In some embodiments, second coupling portion 24b may be in the form of a telescoping feature or nested tubes slidingly disposed with one another.

Second linear link 22d is connected to second leg 22b2 of L-shaped link 22b. A third axis "X3" (see FIG. 2), perpendicular to first axis "X1" and parallel with second axis "X2," is defined through second linear link 22d and second leg 22b2 of second L-shaped link 22b. Second linear link 22d is movable relative to second leg 22b2 of second L-shaped link 22b along third axis "X3." Base 20 includes a third coupling portion 24c, similar to second coupling portion 24b, interconnecting second linear link 22d and second leg 22b2 of second L-shaped link 22b such that relative positions of second linear link 22d and second leg 22b2 of second L-shaped link 22b can be selectively adjusted. In some embodiments, third coupling portion 24c may be in the form of a telescoping feature or nested tubes slidingly disposed with one another. It is contemplated that links 20a, 20b, 20c, 20d may be variously configured, such as, for example, non-linear, arcuate, tapered, undulating and/or bent.

As mentioned above, support system 10 includes a plurality of posts 40a, 40b, 40c, 40d connected to base 20 and configured to be coupled to a surgical table, such as, for example, surgical table "ST." Each post 40a, 40b, 40c, 40d has a respective first end 40a1, 40b1, 40c1, 40d1, a respective second end 40a2, 40b2, 40c2, 40d2, and defines a respective longitudinal axis "Y" therealong. First ends 40a1, 40b1, 40c1, 40d1 are supported on links 20a, 20b, 20c, 20d, respectively, and second ends 40a2, 40b2, 40c2, 40d2 are each configured to support a respective robotic arm 60a, 60b, 60c, 60d. Robotic arms 60a, 60b, 60c, 60d are designed and adapted to perform surgical operations on a patient "P" lying on surgical table "ST." Robotic arms 60a, 60b, 60c, 60d may each include a surgical instrument 62 having an end effector 64 for performing at least one function. Robotic arms 60a, 60b, 60c, 60d may be driven by electric drives (not shown) disposed in posts 40a, 40b, 40c, 40d that are connected to a control device (not shown).

Support system 10 may include one or more angular encoders or sensors 41 to identify an angle of one or more posts 40a, 40b, 40c, 40d relative to another object, including, but not limited to the base 20, surgical table ST, or patient P. Signals from angular sensor 41 may be used to assist in the proper angular alignment of a post 40 and/or robotic arm 60. Alignment assistance may be given by comparing a desired angular position with an actual angular position obtained from the angular sensor 41 and then providing feedback based on the difference. For example if the signals from angular sensor 41 indicate that post 40 and/or robotic arm 60 are at an overly acute angle, a notification may be triggered and/or transmitted indicating that the angle should be increased. In some instances, the notification may provide a specific recommended angle change or the notification may more generally identify that the post 40 and/or robotic arm 60 is not in a proper angular alignment, such as by activate a warning light, sounding an alarm, and/or displaying a warning message.

First ends 40a1, 40b1, 40c1, 40d1, and second ends 40a2, 40b2, 40c2, 40d2, respectively, of posts 40a, 40b, 40c, 40d are movable relative to one another along respective axes "Y." Second ends 40a2, 40c2 of posts 40a, 40c are each configured to be slidingly coupled to a first rail "R1" (see FIG. 1) of surgical table "ST" that extends along a first side of surgical table "ST." Second ends 40b2, 40d2 of posts 40b, 40d are each configured to be slidingly coupled to a second rail "R2" (see FIG. 1) of surgical table "ST" that extends along a second side of surgical table "ST." Accordingly, with posts 40a, 40b, 40c, 40d attached to surgical table "ST," surgical table "ST" can be raised and/or lowered in a direction parallel to longitudinal axis "Y." In some embodiments, posts 40a, 40b, 40c, 40d include a mechanical drive (not shown), such as, for example, a crank, a motor, a winch, a jack, or the like, configured to drive the axial movement of second ends 40a2, 40b2, 40c2, 40d2 relative to first ends 40a1, 40b1, 40c1, 40d1, to drive a raising and/or lowering of surgical table "ST." It is contemplated that posts 40a, 40b, 40c, 40d are slidingly coupled to first and second rails "R1," "R2" via various coupling mechanisms, such as, for example, a C-shaped hook, magnetic couplings, and the like.

Support system 10 may include one or more linear encoders or sensors 43 to identify the position of one or more of the first ends 40a1, 40b1, 40c1, 40d1, and second ends 40a2, 40b2, 40c2, 40d2, of one or more posts 40a, 40b, 40c, 40d with respect to each other and/or another object. Signals from one or more linear sensors 43 may be used to assist in the proper positioning of one or more of the posts 40a, 40b, 40c, and 40d as a post 40 is slid along a respective rail R1, R2. Positioning assistance may be given by comparing a desired position with an actual position obtained from one or more linear sensors 43 and then providing feedback based on the difference. For example if the signals from linear sensors 43 indicate that post 40 has not been slid to a desired position then a notification may be triggered to indicate that the post 40 should be moved. In some instances, the notification may provide a specific recommended distance to move post 40 or the notification may more generally identify that the post 40 is not in a proper position, such as by activate a warning light, sounding an alarm, and/or displaying a warning message.

Some support systems 10 may include angular sensors 41 and linear sensors 43, though other systems 10 may include only angular sensors 41, only linear sensors 43, or neither angular sensors 41 nor linear sensors 43. Including both angular sensors 41 and linear sensors 43 may provide additional verification of both the angular alignment and proper positioning of one or more posts 40.

With continued reference to FIG. 1, each post 40a, 40b, 40c, 40d includes a first joint 44a, a second joint 44b, and a third joint 44c. Joints 44a, 44b, 44c may have one or more degrees of freedom and be configured, such as, for example, knuckle joints, turnbuckle joints, pin joints, cotter joints, bolted joints, screw joints, welded joints, gimbal joints, or the like. First joint 44a movably connects respective first ends 40a1, 40b1, 40c1, 40d1 and second ends 40a2, 40b2, 40c2, 40d of posts 40a, 40b, 40c, 40d to one another. In one embodiment, first joint 44a is slidingly coupled to rail "R1" of surgical table "ST." In this way, surgical table "ST" can be pivoted (e.g., tilted) between a plurality of orientations.

Second joint 44b of each post 40a, 40b, 40c, 40d provides posts 40a, 40b, 40c, 40d with added degrees of freedom. First ends 40a1, 40b1, 40c1, 40d1 each include a third joint 44c, which pivotably couples posts 40a, 40b, 40c, 40d to links 22a, 22b, 22c, 22d, respectively. Although posts 40a, 40b, 40c, 40d are shown and described as having three joints, it is to be understood that posts 40a, 40b, 40c, 40d may include more or less joints.

In operation, base 20 is positioned to at least partially surround surgical table "ST." Specifically, base 20 is oriented relative to surgical table "ST" such that first legs 22a1, 22b1 of first and second L-shaped links 22a, 22b are adjacent and parallel to a foot or head of surgical table "ST" and second legs 22a2, 22b2 of first and second L-shaped links 22a, 22b and first and second linear links 22c, 22d are adjacent and parallel to respective sides of surgical table "ST." Base 20 can include wheels (not shown) attached to a bottom surface thereof so that base 20 can be rolled to a selected position on floor "F" relative to surgical table "ST." In some embodiments, a cushioned mat (not shown) is attached to base 20 to provide a soft surface on which an operating room staff can stand.

In some instances, the configuration (e.g., a length and/or width) of base 20 may need to be adjusted to correspond to a profile of a particular surgical table. As such, first and second L-shaped links 22a, 22b may be moved relative to one another along first longitudinal axis "X1" to adjust a width "W" of base 20. First linear link 22c may be moved relative to second leg 22a2 of first L-shaped link 22a along second longitudinal axis "X2" to adjust a first length "L1" of base 20. Second linear link 22d may be moved relative to second leg 22b2 of second L-shaped link 22b along the third longitudinal axis "X3" to adjust a second length "L2" of base 20.

With base 20 disposed around surgical table "ST" and in the selected configuration, second ends 40a2, 40c2 or joints 44a of posts 40a, 40b, 40c, 40d are coupled to first rail "R1" of surgical table "ST," and second ends 40b2, 40d2 or joints 44a of posts 40b, 40d are coupled to second rail "R2." Robotic arms 60a, 60b, 60c, 60d are coupled or inserted within second ends 40a2, 40b2, 40c2, 40d2 of posts 40a, 40b, 40c, 40d, respectively. It is contemplated that posts 40a, 40b, 40c, 40d contain a power source and means for communication for robotic arms 60a, 60b, 60c, 60d. Upon coupling posts 40a, 40b, 40c, 40d with first and second rails "R1," R2," surgical table "ST" may be pivoted (e.g., tilted), lowered, and/or raised to a selected position relative to base 20. Lengths "L1" and/or "L2" of base 20 may also be adjusted to slide posts 40a, 40b, 40c, 40d relative to rails "R1" and/or "R2" to a selected position along rails "R1" and/or "R2." Base 20 may be adjusted or reconfigured to have a relatively small overall dimension or foot print, to have a relatively large overall dimension or footprint, or any dimension in between.

Figure 4:
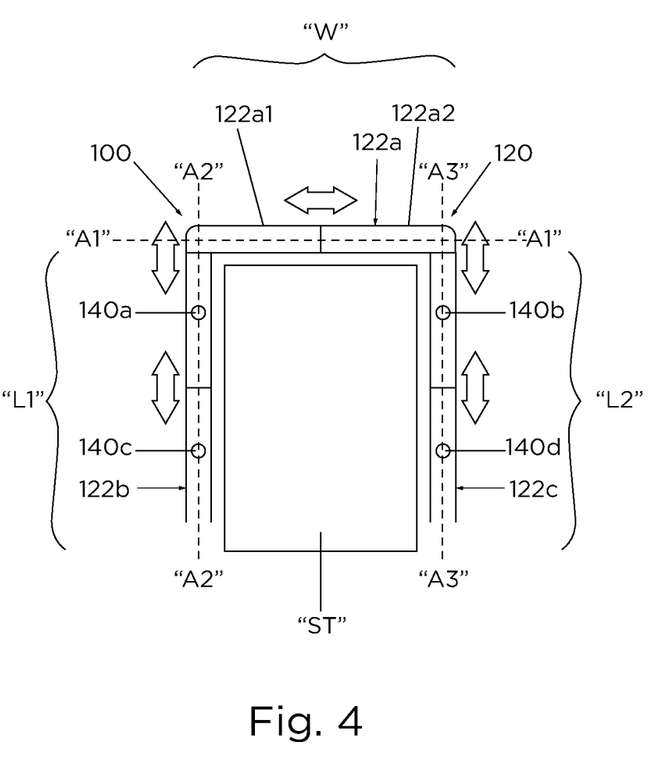
FIG. 4 is a schematic, top view of a second exemplary surgical robotic support system.

With reference to FIG. 4, an alternative surgical robotic support system 100, similar to support system 10 described above with regard to FIGS. 1-3, is provided. Support system 100 includes a base 120 and a plurality of posts 140a, 140b, 140c, 140d, similar to posts 40a, 40b, 40c, 40d discussed above with regard to FIGS. 1-3. Base 120 has a rectangular configuration configured to at least partially surround a surgical table, such as, for example, surgical table "ST."

Base 120 includes a first linear link 122a, a second linear link 122b, and a third linear link 122c. First linear link 122a has a first end 122a1 and a second end 122a2 and defines a first longitudinal axis "A1" therebetween. First and second ends 122a1, 122a2 of first linear link 122a are axially movable relative to one another along first longitudinal axis "A1" to adjust a width "W" of base 20. Second linear link 122b is movably coupled to first end 122a1 of first linear link 122a and defines a second longitudinal axis "A2" therealong. Second longitudinal axis "A2" is perpendicular to first longitudinal axis "A3." Second linear link 122b is axially movable relative to first linear link 122a along second longitudinal axis "A2" to adjust a first length "L1" of base 120. Third linear link 122c is movably coupled to second end 122a2 of first linear link 122a and defines a third longitudinal axis "A3" therealong. Third longitudinal axis "A3" is perpendicular to first longitudinal axis "A1" and parallel to second longitudinal axis "A2." Third linear link 122c is axially movable relative to first linear link 122a along third longitudinal axis "A3" to adjust a second length "L2" of base 120. In some embodiments, each of second and third linear links 122b, 122c include at least two segments that are axially movable relative to one another to adjust the first and/or second lengths "L1," "L2" of base 120.

Posts 140a, 140b, 140c, 140d are configured to be coupled to surgical table "ST." Each post 140a, 140b, 140c, 140d has a first end and a second end. The first ends of posts 140a, 140b, 140c, 140d are supported on second and third links 122b, 122c, respectively. The second ends of posts 140a, 140b, 140c, 140d are each configured to be coupled to a robotic arm 60a, 60b, 60c, 60d.

In operation, base 120 is positioned to at least partially surround surgical table "ST." Specifically, base 120 is oriented relative to surgical table "ST" such that first linear link 122a is adjacent and parallel to a foot or head of surgical table "ST" and second and third linear links 122b, 122c are adjacent and parallel to respective sides of surgical table "ST." In some instances, a configuration (e.g., a length and/or width) of base 120 may need to be adjusted to correspond to a profile of a particular surgical table. As such, first and second ends 122a1, 122a2 of first linear link 122a may be moved relative to one another, along first longitudinal axis "A1," to adjust the width "W" of base 120. Second linear link 122b may be moved relative to first linear link 122a, along second longitudinal axis "A2," to adjust the first length "L1" of base 120. Third linear link 122c may also be moved relative to first linear link 122a, along the third longitudinal axis "A3," to adjust the second length "L2" of base 120.

With base 120 disposed around surgical table "ST" and in the selected configuration, posts 140a, 140c are coupled to a first side of surgical table "ST" and posts 140b, 140d are coupled to the second side of surgical table "ST." Robotic arms 60a, 60b, 60c, 60d are coupled or inserted within the second ends of posts 140a, 140b, 140c, 140d, respectively. Upon coupling posts 140a, 140b, 140c, 140d with surgical table "ST," surgical table "ST" may be pivoted (e.g., tilted), lowered, and/or raised to a selected position. Lengths "L1" and/or "L2" of base 120 may also be adjusted to slide posts 140a, 140b, 140c, 140d relative to the first and/or second sides of surgical table "ST" to a selected position along surgical table "ST."

Figure 5:
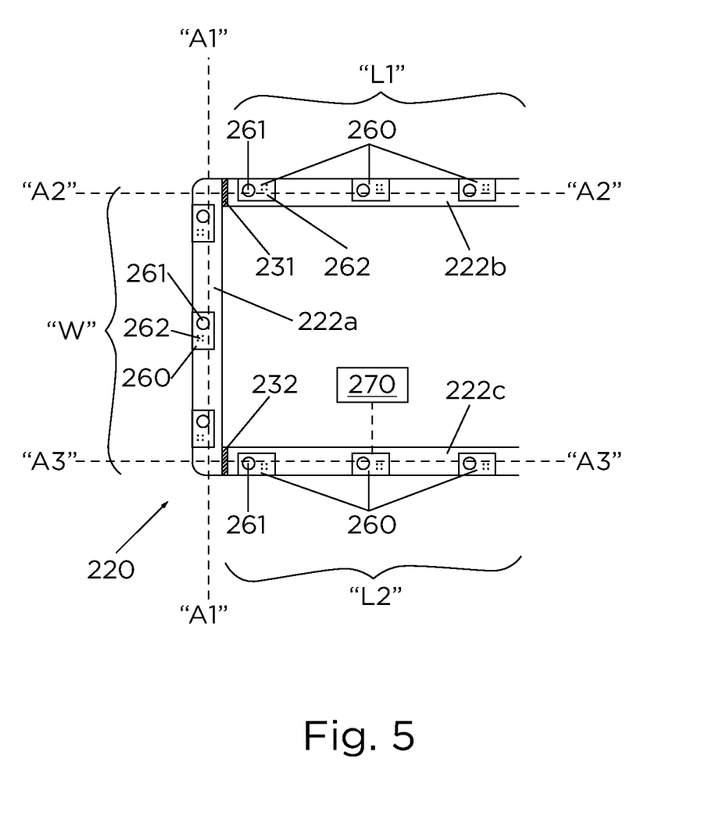
FIG. 5 is a schematic, top view of a third exemplary surgical robotic support system.

With reference to FIG. 5, a second alternative surgical robotic support system 200, similar to support systems 10 and 100 described above with regard to FIGS. 1-4, is provided. Support system 200 includes a base 220 and a plurality of connections 260. Each connection 260 may include mechanical connectivity 261 and/or electrical connectivity 262 between the support system 200 and a respective connected robot arm, such as, for example, robot arms 60a-d shown in FIG. 3.

Mechanical connectivity 261 may include a mechanism, opening, slot, latch, joint, clamp, groove, contour, force, or device that holds the robot arm in a known position relative to its respective connection 260. Each robot arm may include a post, similar to posts 40a-d, that is coupled to a connection 260 via mechanical connectivity 261. A fastener may be used to hold the post in place. The post may also be held in place solely by a frictional force between the post and the base 220 without the need for any extra mechanical fastener.

Electrical connectivity 262 may include electrical conductors, sensors, and/or circuitry for transmitting electrical signals between a connected robot arm and a processing unit 264 coupled to the base 220. Electrical connectivity 262 may include conductors for transmitting power and/or data signals between the robot arm and processing unit 264 of the support system 200 associated with the base 220. These signals may be used to drive the robot arm and/or an instrument (e.g., end effector 64 shown in FIG. 3) attached to the robot arm during surgery. These signals may also contain information used to identify the robot arm, end effector 64, and/or the connection 260 to which the robot arm is coupled. Some signals may also be encoded with data from the robot arm and/or end effector 64 attached to the robot arm and transmitted back to the processing unit 264 of the support system 200. This encoded data may be used by the support system 200 to improve system performance or perform another task.

Figure 6:
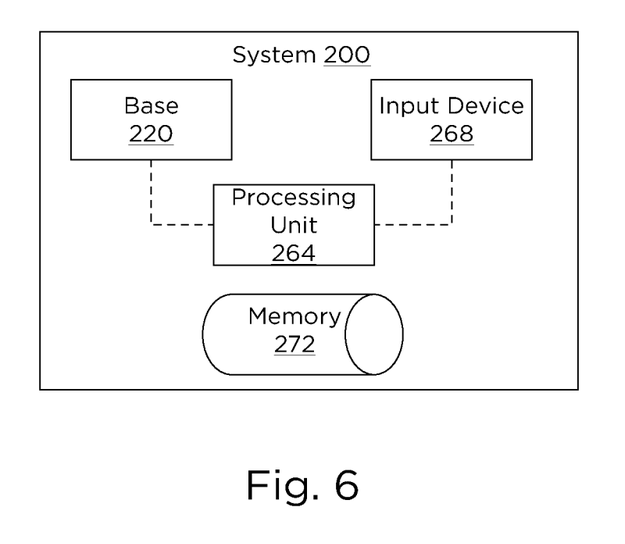
FIG. 6 is an exemplary block diagram.

FIG. 6 shows a block diagram of some components in support system 200. Support system 200 may include a memory 272 configured to store location information of robot arm connections 260. Processing unit 264 may configured to calculate a position of at least two robot arms connected to different robot arm connections 260 from the stored location information in memory 272. Processing unit 264 may be coupled to base 220, memory 272, and input device 268. Processing unit 264 may use information obtained from base 220, memory 272, and/or input device 268 to drive the robot arm and/or an instrument (e.g., end effector 64 shown in FIG. 3) attached to the robot arm during surgery.

Electrical connectivity 262 may also include, or be in the form of, a detector configured to identify the specific connection 260 that a particular robot arm has been connected to. The detector may include a sensor, conductor, and/or circuitry. For example, each robot arm and connection 260 may be assigned unique identifiers that are read by the detector when a robot arm is coupled to a particular connection 260.

In some instances, the electrical connectivity 262 may include a conductor that propagates an electrical signal containing identifying information about the robot arm or the specific connection 260 to which a robot arm is attached. This situation may occur, for example, when the identifying information about the robot arm and/or specific connection 260 to which the robot arm is attached is obtained from a sensor, memory, or other source on the robot arm and then is transmitted from the robot arm to the base through the electrical connectivity 262. Electrical connectivity 262 may also include a transmitter and/or receiver that transmits and/or receives a wired or wireless signal from the robot arm or other source.

A detector may include, or be in the form of, a sensor that detects the coupling of a robot arm to that particular connection 260 and/or uniquely identifies different robot arms. Once the specific connections 260 of each robot arm have been identified, the locations of each of the robot arms relative to the other arms may be calculated. This information may then be used to align movement of an input device 268 (e.g., a computer) with the corresponding movement of an instrument or end effector 64 or image as seen by the surgeon on a display screen from a camera 270 coupled to one of the robot arms.

Support system 200 may include one or more sensors that may sense whether a robot arm has been properly attached to a particular connection 260. These sensors may, but need not be, part of the mechanical connectivity 261 or electrical connectivity 262. A notification about the attachment state of a robot arm to a particular connection 260 may be communicated depending on the signals received from the sensors. For example, if an arm is not properly attached to a particular connection 260, a visual indicator, audible sound, and/or notification message associated with the improper attachment may be triggered to alert a person so that appropriate remedial action may be taken. The visual indicator may be part of a physical device, such as a red/green light located on or near the arm and/or particular connection 260 that indicates whether the arm is properly attached (e.g. green light) or not (e.g. red light), or it may be a virtual, in that a notification message, virtual light, or other indicator is displayed on a display screen.

Base 220 may have a rectangular U-shaped configuration that at least partially surrounds a surgical table, such as, for example, surgical table "ST." Base 220 may include a first modular linear link 222a extending a width W, a second modular linear link 222b extending a length L1, and a third modular linear link 222c extending a length L2 that may be the same or different from length L1.

Each of the modular links 222a-c may be selectively attachable and detachable to the other links 222a-c. For example, link 222a may be attachable to link 222b at attachment point 231 and link 222a may be attachable to link 222c at attachment point 232. In other examples, different attachment points may be provided. First linear link 222a may have a longitudinal axis "A1" that is perpendicular to longitudinal axes "A2" and "A3" of second and third links 222b and 222c respectively. One or more portions of the first linear link 222a may be axially movable relative to one another along first longitudinal axis "A1" to adjust a width "W" of base 220. Similarly, one or more portions of the second and third links 222b and 222c may be axially movable along respective longitudinal axes "A2" and "A3" to adjust the lengths "L1" and "L2" of base 220.

Each link 222 may be coupled to one or more sensors that may sense whether two or more links are properly coupled together. A notification about the coupling state of two or more links may be communicated depending on the signals received from one or more of the sensors about a link coupling state. For example, if one of the links is not properly coupled, a visual indicator, audible sound, and/or notification message associated with the improperly coupled link may be triggered to alert a person about the improper coupling so that appropriate remedial action may be taken. The visual indicator may be part of a physical device, such as a red/green light located near a link that provides status information about the links, or it may be a virtual, in that it that appears as a notification message, virtual light, or other indicator on a display screen.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A surgical robotic arm support system, comprising:
a base including:
first and second modular links configured to be disposed on opposite sides of a surgical table; and
a third modular link extending between respective end portions of the first and second modular links, such that the base is configured to at least partially surround the surgical table; and
a plurality of robot arm connections disposed on at least two of the first, second, or third modular links of the base, each robot arm connection including:
a mechanical connectivity configured to maintain a portion of a connected robot arm at a predetermined position from the base; and
a detector configured to identify at least one of the robot arm connections to which at least one robot arm is connected.

2. The surgical robotic arm support system according to claim 1, wherein each respective mechanical connectivity is configured to restrict movement of at least part of the connected robot arm relative to the base.

3. The surgical robotic arm support system according to claim 2, wherein the electrical connectivity detector of each of the plurality of robot arm connections is disposed between the connected robot arm and the base.

4. The surgical robotic arm support system according to claim 1, further comprising:
a memory configured to store location information of the plurality of robot arm connections; and
a processing unit configured to calculate a position of at least two robot arms connected to different robot arm connections from the stored location information.

5. The surgical robotic arm support system according to claim 4, wherein the processing unit is further configured to align a movement of an input device of thesurgical robotic arm support system with a corresponding movement of an instrument affixed to a robotic arm or a displayed image from a camera coupled to one of the robot arms based on the calculated position.

6. The surgical robotic arm support system according to claim 1, wherein the detector of at least one of the plurality of robot arm connections is configured to identify at least one of the robot arm connections from a unique identifier associated with the at least one robot arm connection.

7. The surgical robotic arm support system according to claim 1, wherein the detector of at least one of the plurality of robot arm connections is configured to detect a robot arm coupling.

8. The surgical robotic arm support system according to claim 7, wherein the detector of the at least one robot arm connection is further configured to identify a particular robot arm coupled to the at least one robot arm connection.

9. The surgical robotic arm support system according to claim 1, wherein the third modular link defines a longitudinal axis that is perpendicular to respective longitudinal axes defined by the first and second modular links when the first, second, and third modular links are attached together.

10. The surgical robotic arm support system according to claim 9, wherein at least one of the first, second, or third modular links is axially movable along its respective longitudinal axis to adjust a dimension of the base.

11. The surgical robotic arm support system according to claim 10, wherein each of the first, second, and third modular links is axially movable along their respective longitudinal axes to adjust at least a width and a length of the base, at least one of the first, second, or third modular links associated with a position sensor configured to detect a movement thereof.

12. A method of using a surgical robotic arm system, comprising:
    positioning first and second modular links of a base on opposite sides of a surgical table;
    positioning a third modular link of the base at an end of the surgical table, the third modular link interconnecting respective end portions of the first and second modular links, such that the first, second, and third modular links at least partially surround the surgical table;
    connecting a pair of surgical robotic arms to a pair of robotic arm connections, the pair of robotic arm connections disposed on at least two of the first, second, or third modular links of the base; and
    identifying, with a detector, the pair of robotic arm connections to which the pair of surgical robotic arms is connected.

13. The method according to claim 12, further comprising mechanically restricting movement of at least part of the pair of connected robotic arms relative to the base.

14. The method according to claim 13, further comprising enabling electrical connectivity between the pair of connected robotic arms and the base.

15. The method according to claim 12, further comprising calculating a position of the pair of robotic arms connected to different robotic arm connections from stored location information about the robotic arm connections.

16. The method according to claim 15, further comprising aligning a movement of an input device with a corresponding movement of an instrument or camera affixed to one of the connected robotic arms based on the calculated position.

17. The method according to claim 15, further comprising identifying, with the detector, each of the connected robotic arms and the robot arm connection to which each identified robotic arm is connected.

18. The method according to claim 12, further comprising:
    axially moving at least one of the first, second, or third modular links along its respective longitudinal axis to adjust a dimension of the base relative to the surgical table; and
    detecting a movement of at least one of the first, second, or third modular links by a position sensor.

19. The method according to claim 18, further comprising:
    processing a signal from the position sensor;
    identifying from the processed position sensor signal an amount of detected movement;
    comparing the identified amount of detected movement to a threshold value; and
    triggering a notification when the compared amount exceeds the threshold value.

20. The surgical robotic arm support system according to claim 1, wherein each of the plurality of robot arm connections is directly connected to the base.

21. The method according to claim 12, further comprising connecting a third surgical robotic arm to the base, such that each of the first, second, and third modular links has a respective surgical robotic arm extending therefrom.

* * * * *